US011419522B2

(12) United States Patent
Bassez et al.

(10) Patent No.: US 11,419,522 B2
(45) Date of Patent: Aug. 23, 2022

(54) DEVICE FOR MEASURING A MEASUREMENT

(71) Applicant: LABORATOIRES INNOTHERA, Arcueil (FR)

(72) Inventors: Sophie Bassez, Villebon sur Yvette (FR); Amina Ouchene, Créteil (FR); Jean-Christophe Lourme, Villejuif (FR); David Renout, Paris (FR)

(73) Assignee: LABORATOIRES INNOTHERA, Arcueil (FR)

( * ) Notice: Subject to any disclaimer, the term of this patent is extended or adjusted under 35 U.S.C. 154(b) by 102 days.

(21) Appl. No.: 16/765,054

(22) PCT Filed: Nov. 13, 2018

(86) PCT No.: PCT/EP2018/081063
§ 371 (c)(1),
(2) Date: May 18, 2020

(87) PCT Pub. No.: WO2019/096778
PCT Pub. Date: May 23, 2019

(65) Prior Publication Data
US 2021/0361187 A1      Nov. 25, 2021

(30) Foreign Application Priority Data
Nov. 16, 2017   (FR) ...................... 1760802

(51) Int. Cl.
*A61B 5/107* (2006.01)
*G01B 3/1069* (2020.01)
(Continued)

(52) U.S. Cl.
CPC .............. *A61B 5/1072* (2013.01); *A41H 1/02* (2013.01); *G01B 3/1048* (2020.01); *G01B 3/1069* (2020.01); *G01B 3/1094* (2020.01)

(58) Field of Classification Search
None
See application file for complete search history.

(56) References Cited

U.S. PATENT DOCUMENTS 2,129,582 A * 9/1938 Johansson ............ G01B 3/1084
                                                          33/555.4
3,832,780 A * 9/1974 Lewis ...................... A41H 1/02
                                                          33/2 R
(Continued)

FOREIGN PATENT DOCUMENTS

AT         5 740 U1      11/2002
FR       2 788 957 A1     8/2000
(Continued)

OTHER PUBLICATIONS

"AMRX-1510 Ultra-slim Scroll Wheel with 5-way Switch Data Sheet"; Avago Technologies; 2007; Retrieved from the Internet; URL: http://www.farnell.com/datasheets/26726.pdf?_ga=2.153910840. 1096437493.1529618863-2064766949.1529618863; Retrieved Jun. 25, 2018.
(Continued)

*Primary Examiner* — Christopher W Fulton
(74) *Attorney, Agent, or Firm* — Oliff PLC

(57) ABSTRACT

A device for measuring a dimension includes: an electronic tape measure including: a portable casing including an opening having a Y axis; a winder in the casing having an X axis; a tape passing through the casing opening and including an end fixed on the winder and a free end outside the casing; a module for measuring a measurement relating to said outer section; a trigger for generating a signal by the trigger activation; and an interpretation module for controlling inputting of the measurement when the trigger signal is received, in which device the free end of the outer section includes a fastener, and the casing includes a fastening region allowing the fastener to be fixed, the length of the
(Continued)

surface of the casing that extends between the fastening region and the opening of the casing being less than 4 cm.

17 Claims, 2 Drawing Sheets

(51) Int. Cl.
*G01B 3/1094* (2020.01)
*G01B 3/1048* (2020.01)
*A41H 1/02* (2006.01)

(56) References Cited

U.S. PATENT DOCUMENTS

| | | | | |
|---|---|---|---|---|
| 5,367,785 | A * | 11/1994 | Benarroch | E05B 67/006 |
| | | | | 33/755 |
| 5,950,321 | A * | 9/1999 | Pena | E04D 13/00 |
| | | | | 33/758 |
| 6,415,199 | B1 * | 7/2002 | Liebermann | A41H 1/02 |
| | | | | 33/512 |
| 6,817,110 | B2 * | 11/2004 | Bohnengel | G01B 3/1056 |
| | | | | 33/511 |
| 7,131,215 | B2 * | 11/2006 | Kang | G01B 3/1041 |
| | | | | 33/769 |
| 8,381,411 | B2 * | 2/2013 | DeLaRosa | G01B 3/1056 |
| | | | | 33/770 |
| 10,349,867 | B2 * | 7/2019 | Bassez | G01B 3/1003 |
| 10,765,345 | B2 * | 9/2020 | Kang | A61B 5/002 |
| 11,147,475 | B2 * | 10/2021 | Harfouche | G01B 3/1005 |
| 2004/0040170 | A1 | 3/2004 | Sanoner | |
| 2007/0068272 | A1 * | 3/2007 | Houser | A61B 5/445 |
| | | | | 73/774 |
| 2011/0258869 | A1 * | 10/2011 | Bittkowski | A61B 5/107 |
| | | | | 33/512 |
| 2015/0308807 | A1 * | 10/2015 | Rhoden | G01B 3/1061 |
| | | | | 33/763 |

FOREIGN PATENT DOCUMENTS

| | | | | |
|---|---|---|---|---|
| GB | 2492805 A * | 1/2013 | | G01B 5/02 |
| JP | H04-89501 A | 3/1992 | | |
| WO | 2007/035960 A2 | 3/2007 | | |
| WO | WO-2019048005 A1 * | 3/2019 | | G01B 3/1084 |

OTHER PUBLICATIONS

Feb. 4, 2019 Search Report issued in International Patent Application No. PCT/EP2018/081063.
Jun. 25, 2018 Search Report issued in French Patent Application No. 1760802.

\* cited by examiner

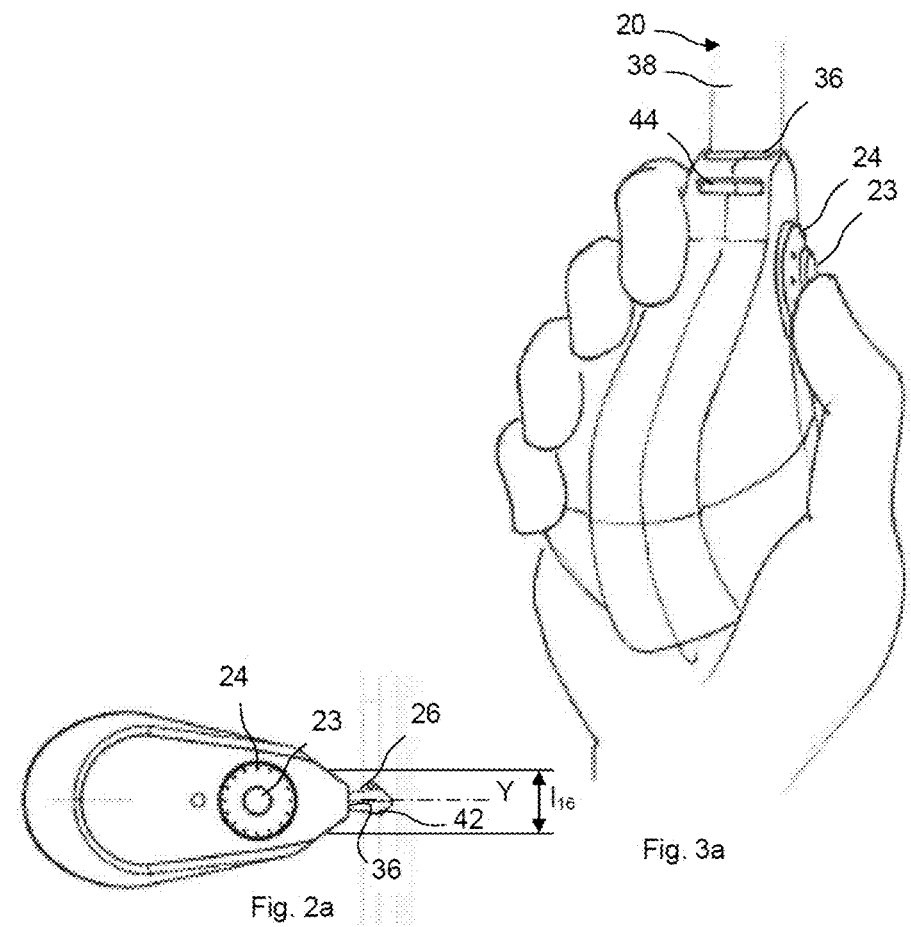
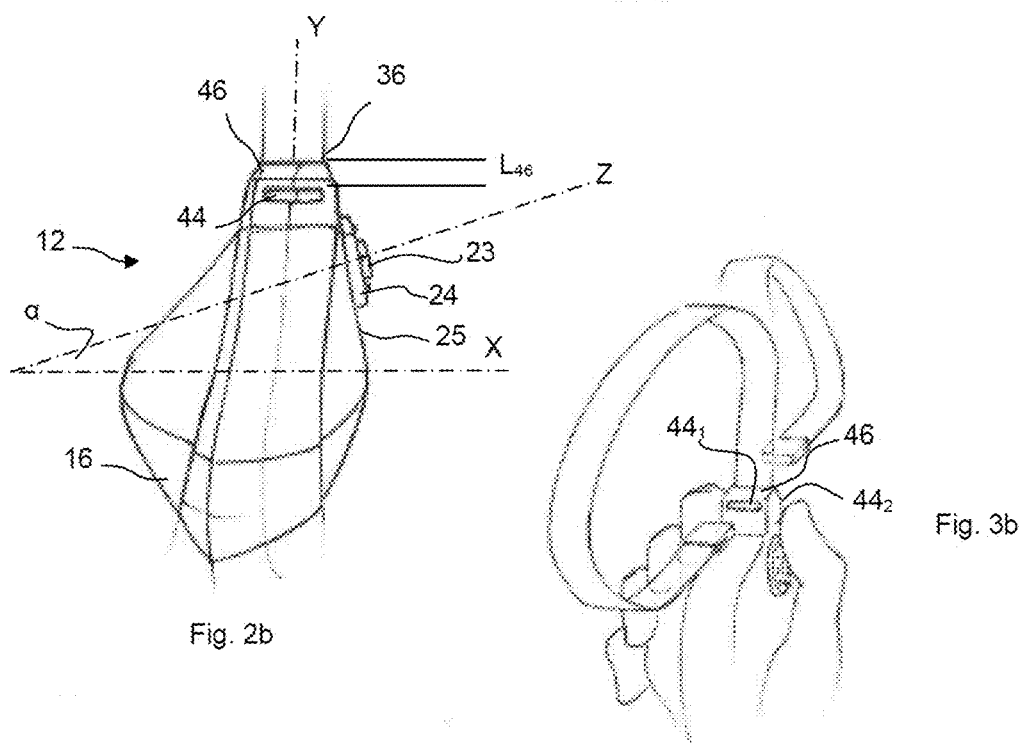
Fig. 3a
Fig. 2a
Fig. 2b
Fig. 3b

DEVICE FOR MEASURING A MEASUREMENT

TECHNICAL FIELD

The invention relates to a device for measuring a dimension of a body part of a patient with a view to a prescription for an elastic venous compression orthosis, or EVC, that is recommended in the event of venous insufficiency of a lower limb of a patient.

PRIOR ART

Elastic venous compression orthoses, formerly known as "compression stockings (or socks)" or "compression tights", are textile medical devices producing a therapeutic effect by compressing the lower limbs, as opposed to "retention stockings" (or even "support stockings" or "anti-fatigue stockings") and to "fashion stockings", which are not medical devices intended for therapeutic use.

Elastic venous compression orthoses are designed to produce a therapeutic effect by compressing the lower limb over a fairly wide area, commonly with a compression profile that decreases toward the top from the ankle.

Since the morphology of the lower limbs is different from one patient to another, an orthosis model is conventionally available in several sizes in order to satisfy the market.

In order to determine the size of an elastic venous compression orthosis intended for a patient, different dimensions of their leg need to be measured, and in particular measurements of heights and perimeters at different altitudes. In particular, the measurements can be taken at standardized altitudes.

The measurements must be taken with the patient in a standing position, which can be uncomfortable for the operator.

In order to measure a perimeter, a conventional tape measure can be used. The quality of the measurement nevertheless depends on the operator responsible for this measurement.

Document FR 2788957 proposes an electronic measuring device. This device particularly comprises an encoder capable of assessing, without the intervention of the operator, a length of an outer section of the tape. This device reduces the risk of error.

However, a permanent requirement exists for improving the effectiveness and the precision of the measurements that are taken in order to prescribe an orthosis.

An aim of the present invention is to address this requirement.

SUMMARY OF THE INVENTION

The invention proposes a device for measuring a dimension, and in particular a perimeter and/or a height dimension of a body part of a patient, said device comprising:
  an electronic tape measure comprising:
    a portable casing comprising a casing opening having a Y axis, which opening preferably is in the form of a slot;
    a winder housed in the casing having an X axis;
    a tape passing through the casing opening and comprising an end fixed on the winder and a free end outside the casing, the section of the tape outside the casing being referred to as "outer section";
    a module for measuring a measurement relating to said outer section;
    a trigger configured to generate a trigger signal as a result of the activation of said trigger by an operator; and
    an interpretation module configured to control the inputting of said measurement in response to the reception of said trigger signal.

According to a first main aspect of the invention, the free end of the outer section comprises a fastener, preferably magnetic, and the casing comprises a fastening region allowing said fastener to be fixed, the length of the surface of the casing that extends between the fastening region and the casing opening, or "contact surface", being less than 4 cm, preferably less than 3 cm, preferably less than 2 cm, preferably less than 1 cm, preferably less than 0.5 cm. Preferably, the fastening region is adjacent to the casing opening, i.e. said distance is zero.

As will be seen in greater detail in the remainder of the description, in a "measuring" position, i.e. when the outer section surrounds a limb of a patient in order to measure the perimeter thereof and when, to this end, the fastener is fixed on the fastening region, the flexible outer section of the tape perfectly adapts to the limb, irrespective of its curvature radius, unlike the contact surface. Since the length of the contact surface is limited, the precision of the measurement is advantageously improved.

According to a second main aspect of the invention, the measuring device comprises an input computer configured to have, successively or simultaneously, a set of input fields intended for inputting said measurements, and the tape measure comprises a thumb wheel communicating with the input computer so that a rotation of said thumb wheel modifies the active input field, an input field being "active" when a measurement can be entered therein.

As will be seen in greater detail in the remainder of the description, such a thumb wheel advantageously allows the operator to modify the active input field, simply by rotating the thumb wheel. Inputting a plurality of measurements is advantageously considerably faster.

Preferably, the positions of the thumb wheel are indexed; the selection of an input field is thus facilitated.

More preferably, the thumb wheel is in the form of a ring surrounding the trigger, which improves the ergonomics. In particular, the operator can thus, with the same finger, turn the thumb wheel and activate the trigger.

According to a third main aspect of the invention, the device comprises a mobile computer, preferably a tablet or a telephone, preferably a tablet, communicating with the measuring module, preferably via Bluetooth®.

As will be seen in greater detail in the remainder of the description, a mobile computer allows the operator to easily communicate with the tape measure, even when the tape measure is used in an uncomfortable position, for example, to measure an ankle perimeter. The risk of measurement error is advantageously reduced.

Furthermore, the computation capabilities on board the tape measure can be reduced and at least partially assumed by the mobile computer. Advantageously, the manufacturing cost of the tape measure is reduced.

Preferably, the mobile computer comprises an input computer.

In a preferred embodiment, the input computer comprises a touch screen and is configured so that pressing a finger on a zone of the screen representing an input field selects this field.

In a preferred embodiment, the device also comprises a fixed computer, able to communicate with the mobile computer, preferably via W-Fi or via Bluetooth®, and connected to the internet.

Advantageously, the fixed computer can be used to define a set of measurements to be taken and to control the mobile computer, so that it successively, or preferably, simultaneously, displays input fields relating to said measurements.

According to a fourth main aspect of the invention, the width of the casing, measured perpendicular to the Y axis, increases when said casing is observed along the X axis and when moving away from the casing opening along the Y axis. In other words, in a plane perpendicular to the X axis, the outer dimensions of the casing, measured perpendicular to the Y axis, decrease on the approach to the casing opening.

As will be seen in greater detail in the remainder of the description, the tapered shape of the casing in the vicinity of the casing opening facilitates taking measurements in difficult to access regions.

According to a fifth main aspect of the invention, the winder is mounted to freely rotate in a winding direction of the tape.

In other words, the tape measure does not comprise any blocking means, for example, a catch, preventing, even temporarily, the winder from rotating in the winding direction of the tape when the tape is unwound.

As will be seen in greater detail in the remainder of the description, the operator therefore cannot block, in any unwinding position, the outer section. The risk of measurement error is advantageously reduced.

According to a sixth main aspect of the invention, the interpretation module is configured to, as a function of said trigger signal, control the inputting of the measurement or to control the deletion of a previous input.

Preferably, the interpretation module is also configured to, as a function of said trigger signal, confirm an input, and/or confirm a set of inputs, and/or delete a set of previous inputs.

As will be seen in greater detail in the remainder of the description, the interpretation module thus allows rapid interaction between the device and the operator. It allows the effectiveness of taking a series of measurements on the same patient to be considerably accelerated.

However, this embodiment is not preferred since it involves training the operator so that they are aware of the convention by which the interpretation module interprets the trigger signal.

In a preferred embodiment, the interpretation module is configured to control the inputting of a measurement each time a trigger signal is received.

According to a seventh main aspect of the invention, the tape has first and second faces with different appearances, preferably with different colors.

As will be seen in greater detail in the remainder of the description, the difference in appearance between the faces facilitates the detection of any twisting of the tape by the operator.

According to an eighth main aspect of the invention, the tape lacks measuring scales, i.e. adapted for measuring said dimension, and in particular lacks a metric or inch scale.

As will be seen in greater detail in the remainder of the description, the absence of such scales forces the operator to use the measurement determined by the measuring module.

In a preferred embodiment, the tape nevertheless has markings that are adapted for setting and/or calibrating.

Of course, the features of the various main aspects of the invention can be combined.

A device according to the invention can further comprise one or more of the following preferred optional features:
said fastener and/or the fastening region is (are) magnetized;
the tape measure comprises means for continuously maintaining a winding force on the outer section and/or a guide designed to guide the winding of the tape;
the fixed computer is configured to allow the selection, by an operator, of an input form associated with a type of orthosis, for example, "stocking", "thigh stocking", "sock", and/or with a treatment to be administered to the patient;
the fixed computer is configured to determine, as a function of the one or, preferably, more completed inputs, at least one elastic venous compression orthosis model adapted to the patient and to the treatment intended for the patient, or "adapted model", and/or at least one orthosis size adapted to the patient and to the treatment intended for the patient, or "adapted size";
the fixed computer is configured so as to present said at least one adapted model and/or said at least one adapted orthosis size to an operator;
the fixed computer is configured so as to present the one or more adapted models and/or the one or more adapted sizes and, preferably, to allow selection, by the operator, of a model and/or a size from among the models and sizes that are presented and, more preferably, to allow at least one orthosis according to said selection to be ordered;
the interpretation module is disposed in the casing or in the mobile computer;
the trigger is a pushbutton;
the tape comprises anti-twist means, preferably a core coated with a layer made of a hypoallergenic material, with the core being stiffer than said layer.

The invention also relates to a method for taking a measurement on a body part of a patient by means of a device according to the invention. Preferably, the method comprises the following steps:
a) independently of steps b) to c):
preferably, selecting an input form comprising a set of input fields each relating to a measurement that the operator wishes to perform, and said input form being presented, preferably, according to the third main aspect of the invention, by the mobile computer;
activating an input field, preferably by means of the mobile computer and, more preferably, according to the second main aspect of the invention, by means of the thumb wheel;
b) applying the contact surface of the casing onto said body part;
c) partially unwinding the tape, surrounding said body part with the tape and the contact surface of the casing and, preferably, according to the first main aspect of the invention, fixing the fastener to the fastening region;
d) activating the trigger and interpreting, by the interpretation module, the trigger signal transmitted by the trigger, optionally according to the sixth main aspect of the invention;
e) processing, as a function of said interpretation, the measurement measured by the measuring module.

Finally, the invention relates to a method for determining a model and/or a size of an elastic venous compression orthosis, said method comprising the following successive steps:

A) inputting a set of measurements taken, on a patient and by an operator, by means of a measuring device according to the invention, the set of measurements preferably comprising at least one measurement of a calf perimeter and of an ankle perimeter, and preferably a measurement of a thigh perimeter and/or of a hip perimeter;

B) searching, in a models base, one or more orthosis models, called "adapted models", and, for each adapted model, one or more sizes, called "adapted sizes", responding to said set of measurements and, preferably, to a therapeutic treatment to be administered to the patient, then presenting the operator, preferably on the fixed computer, with said adapted models and adapted sizes;

C) preferably, selecting, preferably by the operator, preferably on the fixed computer, an adapted model and an adapted size;

D) preferably, sending an order, to a supplier, for an orthosis of the adapted model and of the adapted size selected in the previous step, preferably by means of the fixed computer.

Definitions

An "orthosis" is understood to be an "elastic venous compression orthosis".

The "altitude", or "level", corresponds to a level in the vertical direction when the orthosis is worn by a patient standing up straight, as shown in FIG. 7 of French standard NF G 30-102, section B, which represents a "Hohenstein type" leg model.

"Tape" is conventionally understood to mean a long and narrow strip. In the present description, a "tape" also includes a wire.

A "patient" is not limited to a human being but includes any animal.

A size of an orthosis "responds" or "corresponds" to a set of measurements taken on a patient when the dimensions of this orthosis are adapted to the therapeutic treatment intended for this patient.

An "input field" is an element shown on a computer screen in which information, in particular a measurement, can be entered. An input form comprises a plurality of input fields for a plurality of respective measurements to be taken, preferably for the same patient. Only one input field is "active", i.e. allows, at a given instant, a measurement to be entered. An input field can be activated by clicking in this field. In one embodiment, rotating the thumb wheel allows the active input field to be changed. Preferably, the input field of an active form has a specific appearance. For example, it can be shown in a particular color.

The term "input/entry" is understood to mean the introduction of a measurement in an input field. An input can be manual or automatic. In particular, in a preferred embodiment of the invention, inputting a measurement in an active input field is achieved only by activating the trigger by the operator.

A "thumb wheel" is a component rotationally mounted on the casing.

A thumb wheel is referred to as "indexed" when it only allows, during a complete revolution, a limited number of stable angular positions. Conventionally, by turning the thumb wheel, the operator must exert a force in order to leave each of the stable angular positions, whether they turn the thumb wheel in one direction or in the other direction. In one embodiment, the operator hears a click upon each change of stable angular position, with the click being able to be produced by the tape measure or the mobile computer.

The term "computer" is understood to be any computer processing unit allowing one-way or, preferably two-way, communication with an operator, in particular by voice or by means of a keyboard. A mobile telephone, a tablet, a portable computer, a personal computer (PC) equipped with a screen are examples of computers. A computer can be "fixed" or "mobile" depending on whether it is intended to remain in place or to be transported, respectively. Typically, a mobile computer is a computer weighing less than 1 kilogram, preferably less than 500 grams.

"Base" is understood to be a "database".

A "models base" is a database containing "model files", with a model file containing data relating to an orthosis model. Each model can be available in several sizes. The model files are used to verify whether or not a model and a size of a model are suitable for the requirements of a patient.

A "patient base" is a database containing "patient files". A patient file preferably contains information relating to the patient (coordinates and measurements of the patient in particular), but also, preferably, information relating to the treatment to be administered to the patient. The information relating to the treatment to be administered to the patient can include information relating to the nature of the venous insufficiency, but also relating to the choices of the patient, for example, specifying that the patient would like a stocking or a sock. This data is used to verify whether a model and/or a size are suitable for the requirements of a patient.

A "pathologies base" is a base referencing various pathologies relating to venous insufficiencies and containing information relating to the treatments for these pathologies.

A "stock base" is a database referencing the orthoses available to the operator and/or the deadlines for them to be available to the operator.

Unless otherwise indicated, "comprising", "including", "having", or the variations thereof correspond to a non-exclusive inclusion.

BRIEF DESCRIPTION OF THE FIGURES

Further features and advantages of the invention will become more clearly apparent upon reading the following detailed description, and with reference to the accompanying drawings, in which:

FIG. 2 (FIGS. 2a and 2b) schematically shows a tape measure of a device according to the invention in a preferred embodiment of the invention, shown as a top view and as a bottom view, respectively; and FIG. 3 (FIGS. 3a and 3b) shows the use of the tape measure of FIG. 2.

Figure 1:
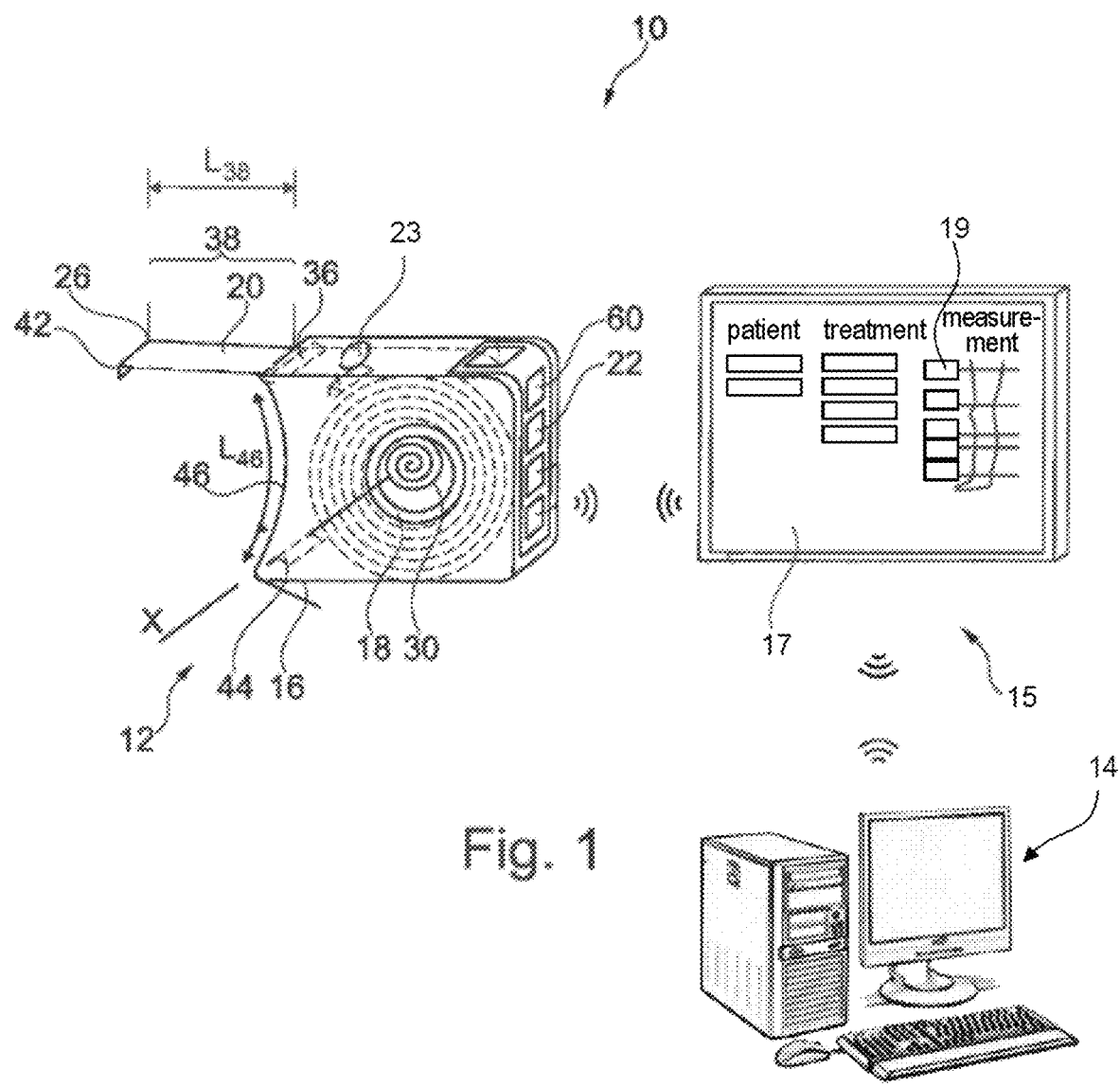
FIG. 1 schematically shows a device according to the invention.

In the various figures, identical or similar components will be referenced in the same manner.

DETAILED DESCRIPTION

Device

FIG. 1 schematically shows a measuring device 10 according to the invention comprising a portable electronic tape measure 12, a fixed computer 14 and a mobile computer 15.

The tape measure 12, the fixed computer 14 and the mobile computer 15 are separated and provided with means for communicating together, and preferably with an operator, preferably via W-Fi between the fixed computer and the mobile computer and preferably via Bluetooth® between the tape measure and the mobile computer. Advantageously, the communication between the tape measure and the mobile computer is thus possible without a Wi-Fi network.

All the conventional communication means are nevertheless contemplated. Communication with the operator particularly can be by voice or by means of a keyboard.

The fixed and mobile computers are preferably conventional electronic tools, particularly comprising a screen, a processor, a computer memory and software. The software conventionally comprises code instructions allowing, when these instructions are executed by the processor, the desired functions to be obtained.

Furthermore, the fixed computer is preferably configured to allow an input form 17 to be selected by the operator and to allow this form to be transmitted to the mobile computer. To this end, it particularly can have access to a patient base and to a pathologies base.

For example, depending on the treatment, the input form can have input fields for measurements of the ankle and/or of the calf and/or of the thigh. In one embodiment, the input form is always the same, regardless of the patient or the treatment.

In a preferred embodiment, the fixed computer is also configured to receive the input forms from the mobile computer in which the input fields have been at least partially filled in with a set of measurements.

Preferably, it has access to a models base and is configured to determine at least one orthosis model and/or size corresponding to said set of measurements, and preferably, the therapeutic treatment intended for the patient.

Preferably, the fixed computer is also configured to display these orthosis sizes and/or models.

In one embodiment, the fixed computer also has access to a stock base and is configured to present the available orthosis models and sizes to the operator, for example, by specifying the number of orthoses available in stock and/or the delivery deadline, and/or to only present the operator with the orthosis models and sizes that are available in stock.

Finally preferably, the fixed computer is configured so that the operator can place an order for at least one orthosis by selecting an orthosis model and size for this model.

The mobile computer particularly can be a telephone or a tablet provided with a suitable application. A tablet is preferred. As a minimum, the mobile computer preferably comprises a touch screen.

Preferably, the mobile computer acts as a computer for inputting measurements relating to the patient and/or to their treatment.

The tape measure 12 conventionally comprises a casing 16, a winder 18 housed in the casing having an X axis, a tape 20 partially wound over the winder 18, a measuring module 22 and a trigger 23.

The tape 20 is intended to surround a body part of a patient, in particular a lower limb, in order to measure a perimeter dimension. The tape 20 preferably has a width of more than 1 cm and/or less than 5 cm, and/or a thickness of less than 1 mm, and/or a length of more than 1 m.

The tape 20 preferably comprises anti-twist means adapted to elastically reduce any twisting of the tape. In particular, the tape can comprise a core coated with a layer made of a hypoallergenic material, with the core being stiffer than said layer so as to limit the risk of twisting.

In order to further reduce the risk of twisting, the tape preferably has first and second faces with different appearances. In particular, the first and second faces can be monochrome and have different colors. Any twisting by a half-turn when taking a measurement thus can be detected immediately.

The tape nevertheless can have first and second faces with identical appearances, or which only differ in that only one of the faces has setting markings.

In one embodiment, the tape has measuring scales, for example, in centimeters or in inches. Advantageously, the operator can thus approximately assess the length of the outer section simply by reading the scales and, where necessary, verify that the electronic measurement provided by the tape measure is consistent with their observations.

In a preferred embodiment, the tape nevertheless does not have a measuring scale. Advantageously, the operator is thus forced to only take into account the measurement determined by the device according to the invention. The risk of error is reduced.

However, the tape can have markings for setting or calibrating.

Unlike measuring scales, the setting markings are not adapted for taking precise measurements. Preferably, they are separated by more than 5 mm, more than 10 mm, more than 50 mm, or more than 100 mm. They are simply used to verify that the supplied electronic measurement is consistent with the setting marking. For example, a setting marking exists at 10 cm and, when the operator has pulled on the tape until this setting marking has appeared, they can verify that the electronic measurement is definitely 10 cm. Otherwise, they can reset the measuring device.

Preferably, the tape does not have a measuring scale but has setting markings, preferably on only one face of the tape.

The free end of the tape 20 preferably comprises a fastener 42 adapted for temporarily fixing a fastening region 44 of the casing.

Preferably, the fastener 42 and the fastening region 44 engage so as to provide magnetic fixing. In particular, the fastener 42 can comprise a magnet and the fastening region 44 can be made of metal, or vice versa. In one embodiment, the fastener 42 and the fastening region 44 both can be made up of magnets oriented so as to be able to be fixed together.

Preferably, the fastener 42 can only be fixed on the casing in the fastening region 44.

In a preferred embodiment, the casing comprises two fastening regions $44_1$ and $44_2$, preferably extending from each side of the casing opening, preferably symmetrically relative to the casing opening. As shown in FIG. 3b, the tape measure is thus ideally suited for a right-handed or a left-handed operator.

The contact surface 46 is the outer surface of the casing that extends between the slot 36 and the fastening region 44. Its length $L_{46}$, measured in a plane perpendicular to the X axis, is less than 4 cm, particularly in the embodiment of FIG. 2.

The trigger 23, preferably in the form of a button, allows the operator to communicate with the measuring device, and in particular to set the time of the measurement. It is configured so that, when it is activated, it transmits a trigger signal. In one embodiment, the trigger signal depends on the type of activation, for example, it depends on the duration that the trigger is pressed. In a preferred embodiment, the trigger signal is constant, i.e. any activation of the trigger produces the same effect.

In the preferred embodiment shown in FIG. 2, the tape measure also comprises a thumb wheel 24 rotationally mounted about a Z axis. Advantageously, the tape measure thus equally can be used by a right-handed or a left-handed operator.

The axis of rotation Z is preferably substantially perpendicular to the wall 25 of the casing on which the thumb wheel extends. The axis of the thumb wheel nevertheless can be oriented differently and in particular oriented parallel to said wall.

The Z axis is preferably coplanar to the X axis or perpendicular to the X axis, with two axes being perpendicular to each other when the planes that are perpendicular thereto themselves are perpendicular to each other. When the X and Z axes are coplanar, they together form an angle α that is preferably less than 60°, 50°, 40°, even less than 30°, and/or greater than 10°, preferably greater than 20°.

The Z axis preferably extends in a plane of symmetry of the casing.

The thumb wheel 24 is preferably disposed so as to rotate about the trigger 23, which is particularly ergonomic. Preferably, the thumb wheel 24 is indexed and only assumes a limited number of stable angular positions.

Preferably, the thumb wheel does not have a travel limit stop. The rotation of the thumb wheel is then referred to as "free". In other words, it is possible for the thumb wheel to be indefinitely rotated in one direction or in the other direction.

More preferably, the thumb wheel interacts with the input form, so as to activate the input fields of this form in a predefined order. Preferably, when the operator rotates the thumb wheel in one direction until the last input field is reached, an additional rotation in the same direction results in the activation of the first input field. The rotation of the thumb wheel thus allows successive activation of the various input fields "as a loop".

Conventionally, the winder 18 is in the general shape of a drum rotationally movable about its X axis. A first end of the tape 20 is fixed on the cylindrical lateral surface of the winder. The second end, or "free end" 26, of the tape 20 is free and extends outside the casing. A spring 30 tends to cause the winder to rotate in a first direction, called "winding direction". The opposite direction is called "unwinding direction".

In a position called "rest position" (FIG. 2a), nearly all the tape 20 is wound on the winder, with only the free end 26 of the tape 20 extending outside the casing.

The tape exits the casing through a casing opening provided in the casing 16 having a Y axis. The shape of the opening preferably substantially corresponds to the transverse section of the tape. Preferably, the opening is in the form of a slot 36.

The width $I_{16}$ of the casing, measured perpendicular to the Y axis, increases when said casing is observed along the X axis and when moving away from the casing opening along the Y axis. This shape advantageously facilitates the application of the contact surface on fairly inaccessible zones of the body.

Conventionally, the fastener 42 is, in the rest position, in abutment on the edge of the slot 36.

The tape 20 is conventionally unwound by pulling on its free end 26, against the moment exerted by the spring 30 on the winder 18. The section 38 of the tape 20 that extends outside the casing is called "outer section".

Preferably, the tape measure 12 comprises means for continuously maintaining a winding force on the outer section, i.e. tending to wind it around the drum. These means can be formed by the spring 30 when the tape measure 12 does not comprise any means for blocking the outer section of the tape in position, apart from the optional fastener 42 when it is fixed on the fastening region 44. The optional fastener 42 is then the only means for blocking the outer section of the tape.

In one embodiment, the tape measure 12 comprises a brake, which can be activated by the operator, allowing winding of the tape to be slowed down. In one embodiment, the brake only allows winding to be slowed down. In one embodiment, it also allows the tape to be blocked in a position in which it is partially or completely unwound.

More preferably, the casing comprises a guide designed to guide the winding of the tape.

Unlike a mechanical tape measure, the electronic tape measure 12 also comprises a measuring module 22 capable of electronically determining a measurement, and an interpretation module 60 intended to take into account an instruction provided by the operator by means of the trigger 23 in order to control measuring.

The measuring module 22 can comprise, for example, a rotation encoder of the winder 18 or an encoder, for example, an optical or magnetic encoder, detecting and counting markings on the tape 20 or, preferably, on the winder that passes in front of it, as disclosed in FR 2788957.

The measuring module 22 comprises the means for communicating with the fixed computer and/or the mobile computer, preferably at least with the mobile computer.

In a preferred embodiment, the tape measure can only communicate with the mobile computer. Preferably, it does not keep any data relating to the measurements, i.e. it transmits all the measurements and instructions received from the operator to the fixed computer and/or, preferably, to the mobile computer. The complexity of the tape measure and its cost are advantageously reduced.

Preferably, the analysis module continuously takes measurements and these measurements are displayed on the fixed computer and/or the mobile computer, preferably on the mobile computer. Thus, the operator can continuously verify that the device operates correctly.

Manufacturing a measuring device according to the invention does not pose a particular problem.

Operation

The operation of the measuring device 10 flows directly from the aforementioned description.

Conventionally, the operator is a doctor or a pharmacist who must select and order an orthosis for treating a patient. They therefore have to take a set of perimeter measurements on a limb of the patient, for example, a measurement on the ankle, a measurement on the calf and a measurement on the thigh on one leg.

In step a), an input form 17 is selected and shown on the mobile computer.

Preferably, the operator enters a prescription on the fixed computer. The prescription conventionally provides information relating to the patient, and in particular their name, and relating to the treatment, by particularly specifying the nature, the category and the number of orthoses to be ordered. Consequently, the fixed computer determines an input form adapted to the prescription and transmits it to the mobile computer. Similarly, the fixed computer can transmit an instruction to the mobile computer so that the mobile computer extracts an input form from a form base that is adapted to the prescription.

The input form 17 can comprise only the input fields 19 that must be filled in to select an orthosis adapted to the treatment to be administered. Preferably, it nevertheless comprises input fields for each of the measurements likely to be used to select any orthosis. The operator thus can enter measurements that optionally will be useful for a subsequent treatment.

In the input form, the input fields are ordered. For example, the input fields can successively relate to the ankle, the calf, then the thigh. By default, the first input field is active. By modifying the angular position of the thumb wheel, the operator can modify the active input field.

Preferably, the active input field has an appearance that is specific thereto.

Preferably, the input fields are shown next to a drawing of a leg, at the altitude corresponding to the measurement to be taken (FIG. 1).

The operator subsequently proceeds to take the first measurement, for example, the perimeter of the ankle.

They turn on the tape measure.

Preferably, the measuring module is then continuously communicating with the mobile computer and particularly sends the length of the outer section thereto. More preferably, the mobile computer displays a corresponding value in real time.

Preferably, the displayed value depends on the active input field. For example, if the active input field relates to a perimeter, the displayed value is equal to the sum of the length $L_{46}$ of the contact surface and of the length $L_{38}$ of the outer section. If the active input field relates to a height, the displayed value is equal to the length of the outer section.

In one embodiment, the displayed value is equal to the length $L_{38}$ of the outer section and the length $L_{46}$ of the contact surface is displayed so that it can be taken into account by the operator.

By turning the thumb wheel (FIG. 3a), the operator activates the input field relating to the measurement of the ankle perimeter. Preferably, each time the position changes, the thumb wheel 24 transmits a selection signal, which is transmitted to the mobile computer. More preferably, each time a selection signal is received, the mobile computer modifies the active input field, with the order of the successively activated input fields being predefined.

In step b), the operator applies the contact surface 46 onto the ankle.

Step b) also can be performed after the operator has partially unwound the tape (start of step c)).

In step c), they pull on the free end 26 of the tape, which emerges from the slot 36 of the casing, so as to unwind a section of the tape by a sufficient length. They place the tape around the ankle and fasten the fastener 42 on the fastening region 44 of the casing (FIG. 3b).

As they unwind or wind the tape, the operator thus sees the value displayed by the mobile computer change in real-time. They can thus immediately detect a malfunction.

The two faces of the tape preferably have a different appearance. If, while extending around the ankle, the operator twists the tape by a half-turn, they thus immediately observe a difference in appearance between the portion of the tape exiting the slot 36 and that fixed to the fastening region 44. They can thus correct the position of the tape.

The lack of scales advantageously prevents the operator from reading the measurement on the tape as opposed to on the mobile computer. The risk of error is reduced.

The use of magnetic fixing means is particularly advantageous in the main intended application. In particular, the operator can fix the fastener 42 even when they cannot see the fastening region or if it is difficult to see, which is particularly the case when the operator has to measure an ankle perimeter whilst the patient is standing upright. Furthermore, the magnetic means allow rapid fixing, and do not require specific training for the operator. Finally, they allow the location where the fastener 42 must be fixed on the casing to be precisely defined, which further limits the risk of error.

Once the fastener is fixed to the fastening region, the operator releases the tape. With the tape measure 12 not comprising any means for blocking the tape in position, apart from the fastener 42 fixed on the fastening region 44, the tape therefore presses against the ankle, and the risk of measurement error is advantageously reduced.

The value displayed by the mobile computer is then equal to the sum of the length $L_{46}$ of the contact surface and of the length $L_{38}$ of the section of the tape pressed on the ankle. The contact surface is defined by a rigid wall of the casing and therefore is not precisely adapted to the shape of the ankle. This results in a measurement error. The reduced length of the contact surface advantageously limits this error.

In step d) the operator activates the trigger 23 in order to transmit an instruction to the interpretation module 60. More specifically, the trigger sends a trigger signal to the interpretation module 60 so that it can act accordingly.

Preferably, the interpretation module 60 or the trigger emits a warning, preferably a light or audible warning, depending on said instruction. In one embodiment, the emitted warning is similar to the trigger signal.

For example, the warning is an audible signal that lasts for as long as the operator presses the trigger. Advantageously, the operator thus can easily control its operation.

In a preferred embodiment, any activation of the trigger is understood to be an order for entering the value displayed on the mobile computer. The interpretation module 60 then controls the inputting, in the active input field, of the displayed value, i.e. the inputting of the measurement, then, preferably, the activation of the next input field.

In another embodiment, the operator can, by activating the trigger in a particular manner determined by a convention, confirm a set of previous inputs or can delete a previous input or can delete a set of previous inputs.

The convention can be as follows, for example:
a short press on the trigger can mean "input a measurement";
two successive short presses can mean "delete the last input and activate the corresponding input field";
three successive short presses can mean "delete all the input fields from the input form";
a long press, for example, of more than one second, can mean "send the input form to the fixed computer and display the input form of the next patient".

In one embodiment, the convention allows a dialogue to be established between the measuring device and the operator. In other words, in response to a first action by the operator on the trigger, the device transmits a response, to which the operator can respond by again acting on the trigger.

The operator subsequently repeats steps b) to d) to measure the calf perimeter, then the thigh perimeter (step A)).

According to the above example of a convention, if the operator realizes that they have made a mistake affecting all the measurements that have already been entered, they indicate as such by three short presses on the trigger. The interpretation module then deletes all the measurements entered in the displayed input form.

When entering the last measurement, the operator indicates that it is the last measurement for the patient by pressing and holding the trigger. The mobile computer saves the input form and/or, preferably, transfers the measurements that it contains to the fixed computer.

These measurements also can be sent by clicking on a button on the input form that is programmed to this end.

In one embodiment, the doctor or the pharmacist can select an orthosis model and/or size corresponding to the input form that has thus been completed, conventionally by means of a grid. Step B) facilitates this selection.

In step B), the fixed computer compares all the entered measurements with the features of orthoses available in the orthoses models base. It accordingly proposes one or more adapted models and/or one or more adapted sizes for these models, generally one adapted size per model.

Preferably, the fixed computer consults the stock base in order to determine the availability of these models and sizes. Preferably, they show information relating to the delivery deadline for these models and sizes (status of stocks and/or supply lead time in particular).

In one embodiment, the fixed computer only proposes models and/or sizes corresponding to the information relating to the treatment to be administered to the patient.

Preferably, the fixed computer is also configured so that the operator can select, from the proposals made by the fixed computer, a model of a size, and order a corresponding orthosis.

As is now clear, the invention provides solutions allowing the effectiveness of measurements to be improved, and in particular of measurements of perimeter dimensions.

Of course, the invention is not limited to the embodiments described and shown, which are provided for illustrative and non-limiting purposes.

In particular, a device according to the invention also can be used to measure dimensions other than a perimeter dimension, for example, the length of a leg.

It also can be used in other fields of application, for example, to measure an object, in particular for textile manufacturing, for renovating old objects, or for furniture upholstery.

The trigger also can be different from a single button. It particularly can comprise a plurality of buttons, which allows the possible instructions to be multiplied.

Some of the computer processing described as being carried out by the tape measure could be carried out by the mobile computer, and vice versa. In one embodiment, which is not preferred, the mobile computer could be integrated in the tape measure.

Some of the computer processing described as being carried out by the mobile computer could be carried out by the fixed computer, and vice versa.

The fixed computer and the mobile computer even could be merged, preferably in the form of a mobile computer.

The invention claimed is:

1. A device for measuring a dimension, said device comprising:
    an electronic tape measure comprising:
        a portable casing comprising a casing opening having a Y axis;
        a winder housed in the casing having an X axis;
        a tape passing through the casing opening and comprising an end fixed on the winder and a free end outside the casing, the section of the tape outside the casing being referred to as "outer section";
        a module for measuring a measurement relating to said outer section;
        a trigger configured to generate a trigger signal as a result of the activation of said trigger by an operator; and
        an interpretation module configured to control the inputting of said measurement in response to the reception of said trigger signal,
    in which device the free end of the outer section comprises a fastener, and the casing comprises a fastening region allowing said fastener to be fixed, the length of the surface of the casing that extends between the fastening region and the opening of the casing being less than 4 cm,
    wherein the width of the casing, measured perpendicular to the Y axis, increases when said casing is observed along the X axis and when moving away from the casing opening along the Y axis,
    wherein the device comprises an input computer configured to have, successively or simultaneously, a set of input fields intended for inputting said measurements, the tape measure comprising a thumb wheel communicating with the input computer so that a rotation of said thumb wheel modifies the active input field, an input field being "active" when a measurement can be entered therein,
    wherein the axis of rotation of the thumb wheel is coplanar to the X axis, and
    wherein the X axis and the axis of rotation of the thumb wheel together form an angle of more than 10° and of less than 60°.

2. The device according to claim 1, wherein said length is less than 1 cm.

3. The device according to claim 1, comprising two regions, called fastening regions, disposed on each side of the casing opening.

4. The device according to claim 1, comprising a fixed computer configured to determine, as a function of the one or more input measurements, at least one orthosis model for elastic venous compression adapted to the patient and to the treatment intended for the patient, and/or at least one orthosis size adapted to the patient and to the treatment intended for the patient.

5. The device according to claim 1, wherein said fastener and/or the fastening region is (are) magnetized.

6. The device according to claim 1, wherein the tape measure comprises means for continuously maintaining a winding force on the outer section and/or a guide designed to guide the winding of the tape.

7. A method for taking a measurement on a body part of a patient by means of a device according to claim 1, said method comprising the following steps:
    a) independently of steps b) to c):
        selecting an input form comprising a set of input fields each relating to a measurement that the operator wishes to perform, and presenting said input form;
        activating an input field;
    b) applying the contact surface of the casing onto said body part;
    c) partially unwinding the tape, surrounding said body part with the tape and the contact surface of the casing and fixing the fastener to the fastening region;
    d) activating the trigger and interpreting, by the interpretation module, the trigger signal transmitted by the trigger;
    e) processing, as a function of said interpretation, the measurement measured by the measuring module.

8. A device for measuring a dimension, said device comprising:
    an electronic tape measure comprising:
        a portable casing comprising a casing opening having a Y axis;

a winder housed in the casing having an X axis;

a tape passing through the casing opening and comprising an end fixed on the winder and a free end outside the casing, the section of the tape outside the casing being referred to as "outer section";

a module for measuring a measurement relating to said outer section;

a trigger configured to generate a trigger signal as a result of the activation of said trigger by an operator; and an interpretation module configured to control the inputting of said measurement in response to the reception of said trigger signal, in which device the free end of the outer section comprises a fastener, and the casing comprises a fastening region allowing said fastener to be fixed, the length of the surface of the casing that extends between the fastening region and the opening of the casing being less than 4 cm, wherein the tape has first and second faces with different appearances, and/or wherein the tape lacks measuring scales and/or comprises setting or calibrating markings, and the device comprising two fastening regions, disposed on each side of the casing opening.

9. The device according to claim 8, comprising an input computer configured to have, successively or simultaneously, a set of input fields intended for inputting said measurements, the tape measure comprising a thumb wheel communicating with the input computer so that a rotation of said thumb wheel modifies the active input field, an input field being "active" when a measurement can be entered therein.

10. The device according to claim 9, wherein the thumb wheel is in the form of a ring surrounding the trigger.

11. The device according to claim 9, wherein the thumb wheel is free to rotate and is indexed.

12. The device according to claim 9, wherein the axis of rotation of the thumb wheel is coplanar to the X axis.

13. The device according to claim 12, wherein the X axis and the axis of rotation of the thumb wheel together form an angle of more than 10° and of less than 60°.

14. The device according to claim 8, comprising a mobile computer communicating with the measuring module.

15. The device according to claim 14, wherein the measuring module continuously communicates with the mobile computer and sends a length thereto that relates to the outer section, the mobile computer displaying a corresponding value in real time.

16. The device according to claim 15, comprising an input computer configured to have, successively or simultaneously, a set of input fields intended for inputting said measurements, the tape measure comprising a thumb wheel communicating with the input computer so that a rotation of said thumb wheel modifies the active input field, an input field being "active" when a measurement can be entered therein, wherein the displayed value depends on the active input field.

17. The device according to claim 8, wherein the interpretation module is configured to, as a function of said trigger signal, control the inputting of the measurement or to control the deletion of a previous input.

* * * * *